US010906851B2

(12) United States Patent
Rungta et al.

(10) Patent No.: US 10,906,851 B2
(45) Date of Patent: Feb. 2, 2021

(54) PROCESS FOR RECOVERING PARA-XYLENE

(71) Applicants: EXXONMOBIL CHEMICAL PATENTS INC., Baytown, TX (US); GEORGIA TECH RESEARCH CORPORATION, Atlanta, GA (US)

(72) Inventors: Meha Rungta, Houston, TX (US); Robert G. Tinger, Friendswood, TX (US); Jeevan S. Abichandani, Houston, TX (US); Dana L. Pilliod, League City, TX (US); John R. Porter, Friendswood, TX (US); Anthony Go, Houston, TX (US); Sankar Nair, Atlanta, GA (US); Ke Zhang, Medford, MA (US)

(73) Assignees: EXXONMOBIL CHEMICAL PATENTS INC., Baytown, TX (US); GEORGIA TECH RESEARCH CORPORATTON, Atlanta, GA (US)

( * ) Notice: Subject to any disclaimer, the term of this patent is extended or adjusted under 35 U.S.C. 154(b) by 201 days.

(21) Appl. No.: 16/074,220

(22) PCT Filed: Feb. 9, 2017

(86) PCT No.: PCT/US2017/017201
§ 371 (c)(1),
(2) Date: Jul. 31, 2018

(87) PCT Pub. No.: WO2017/146914
PCT Pub. Date: Aug. 31, 2017

(65) Prior Publication Data
US 2020/0181042 A1  Jun. 11, 2020

Related U.S. Application Data

(60) Provisional application No. 62/300,291, filed on Feb. 26, 2016.

(51) Int. Cl.
*C07C 5/27* (2006.01)
*B01D 3/14* (2006.01)
(Continued)

(52) U.S. Cl.
CPC ............ *C07C 5/2775* (2013.01); *B01D 3/143* (2013.01); *B01D 15/185* (2013.01);
(Continued)

(58) Field of Classification Search
CPC ..... C07C 5/2737; C07C 5/2775; C07C 7/005; C07C 7/04; C07C 7/12; C07C 2521/04;
(Continued)

(56) References Cited

U.S. PATENT DOCUMENTS 3,761,533 A   9/1973   Otani et al.
5,705,726 A * 1/1998   Abichandani ............ B01J 29/40
                                                      585/481

(Continued)

FOREIGN PATENT DOCUMENTS

WO   WO-0204391 A1 *  1/2002   ............... C07C 7/13

OTHER PUBLICATIONS

Li et al. ("Metal-Organic Frameworks for Separations" Chem. Rev. 2012, 112, 869-932; see p. 888, "2.2.2. C8 Alkylaromatic Isomers") (Year: 2012).*

(Continued)

*Primary Examiner* — Youngsul Jeong
*Assistant Examiner* — Jason Y Chong
(74) *Attorney, Agent, or Firm* — Roberts Calderon; Safran & Cole P.C.

(57) ABSTRACT

Para-xylene is separated from a mixture of xylenes and ethylbenzene by a separation process. An ortho-selective adsorbent is used to reduce the ortho-xylene concentration of the xylenes, prior to contact of the xylenes and ethylbenzene with a para-selective adsorbent. The stream rich in
(Continued)

ortho-xylene may be isomerized in the liquid phase to increase the amount of para-xylene therein. The para-xylene-depleted stream may be treated in the vapor phase to remove the ethylbenzene and then subjected to isomerization in the liquid phase to produce a stream having a higher than equilibrium amount of para-xylene.

22 Claims, 1 Drawing Sheet

(51) Int. Cl.
*B01D 15/18* (2006.01)
*B01J 20/16* (2006.01)
*B01J 20/22* (2006.01)
*B01J 29/70* (2006.01)
*B01J 35/00* (2006.01)
*B01J 35/10* (2006.01)
*C07C 7/00* (2006.01)
*C07C 7/04* (2006.01)
*C07C 7/12* (2006.01)

(52) U.S. Cl.
CPC .......... *B01D 15/1828* (2013.01); *B01J 20/16* (2013.01); *B01J 20/226* (2013.01); *B01J 29/7046* (2013.01); *B01J 35/006* (2013.01); *B01J 35/1014* (2013.01); *C07C 5/2737* (2013.01); *C07C 7/005* (2013.01); *C07C 7/04* (2013.01); *C07C 7/12* (2013.01); *C07C 2521/04* (2013.01); *C07C 2521/08* (2013.01); *C07C 2521/12* (2013.01); *C07C 2529/70* (2013.01)

(58) Field of Classification Search
CPC ............ C07C 2521/08; C07C 2521/12; C07C 2529/70; B01D 3/143; B01D 15/1828; B01D 15/185; B01J 35/006; B01J 35/1014; B01J 29/7046; B01J 20/16; B01J 20/226
See application file for complete search history.

(56) References Cited

U.S. PATENT DOCUMENTS

| | | | |
|---|---|---|---|
| 6,376,733 | B1 | 4/2002 | Ferraro et al. |
| 8,704,031 | B2 | 4/2014 | Kulprathipanja et al. |
| 2002/0068844 | A1 | 6/2002 | Doyle et al. |
| 2012/0004491 | A1 | 1/2012 | Kulprathipanja et al. |
| 2015/0299071 | A1 | 10/2015 | Ou et al. |

OTHER PUBLICATIONS

International Search Report and Written Opinion issued in the corresponding application No. PCT/US2017/017201 dated Apr. 26, 2017.

* cited by examiner

PROCESS FOR RECOVERING PARA-XYLENE

CROSS-REFERENCE TO RELATED APPLICATIONS

The present application is a U.S. National Phase of PCT/US2017/017201 filed on Feb. 9, 2017 claiming priority to provisional U.S. Patent application No. 62/300,291 filed Feb. 26, 2016. The disclosure of the PCT Application is hereby incorporated by reference into the present Application.

PRIORITY

This application claims priority to and the benefit of U.S. Provisional Application No. 62/300,291, filed on Feb. 26, 2016, the disclosure of which is incorporated herein by reference in its entirety.

FIELD OF THE INVENTION

This invention relates to a process for recovering para-xylene from a mixture of xylenes and ethylbenzene. An ortho-selective adsorbent is used to reduce the ortho-xylene concentration of the xylenes, prior to contact of the xylenes and ethylbenzene with a para-selective adsorbent. The ortho-selective adsorbent may be a Metal Organic Framework (MOF) and the para-selective adsorbent may be a zeolite.

BACKGROUND OF THE INVENTION

Ethylbenzene (EB), para-xylene (PX), ortho-xylene (OX) and meta-xylene (MX) are present together in many $C_8$ aromatic product streams from chemical plants and oil refineries. While all these species have important uses, market demand for para-xylene, used extensively as starting material for making synthetic fibers, tends to be greater than for the other $C_8$ aromatic isomers.

Given the higher demand for para-xylene as compared with its other isomers, there is significant commercial interest in maximizing para-xylene production from any given source of $C_8$ aromatic materials. However, there are two major technical challenges in achieving this goal of maximizing para-xylene yield. First, the four $C_8$ aromatic compounds, particularly the three xylene isomers, are usually present in concentrations dictated by the thermodynamics of production of the $C_8$ aromatic stream in a particular plant or refinery. As a result, the para-xylene production is typically limited to the amount originally present in the $C_8$ aromatic stream, which is, again in the typical case, approximately 24 mol % at thermal equilibrium, unless additional processing steps are used to increase the amount of para-xylene and/or to improve the para-xylene recovery efficiency. Secondly, the $C_8$ aromatics are difficult to separate due to their similar chemical structures and physical properties and identical molecular weights.

A variety of methods are known to increase the concentration of para-xylene in a $C_8$ aromatics stream. These methods normally involve a xylene isomerization loop system comprising a separation step, in which at least part of the para-xylene is recovered (and removed from the system in a para-xylene-enriched stream), leaving a para-xylene-depleted stream, the latter being sent to a xylene isomerization step, in which the para-xylene content of the para-xylene-depleted stream is returned back towards thermal equilibrium concentration and recycled to the separation step.

The separation step may be accomplished using fractional crystallization techniques, which are based on the difference on the freezing points of the $C_8$ aromatic isomers, or adsorption separation techniques, which are based on the selectivity of adsorbent for one isomer over another and are typically simulated moving bed (SMB) processes. Amongst the well-known adsorption separation techniques are the UOP Parex™ Process and the Axens Eluxyl™ Process.

A prior art system including the separation step and isomerization steps referred to above generally will include the use of numerous fractionation towers, e.g., a reformate splitter, a benzene recovery tower, a toluene recovery tower, a xylene rerun tower, an isomerization unit heptanizer, and one or more towers associated with the adsorption separation unit. A system comprising a Parex™ or Eluxyl™ adsorptive separation unit using PDEB (para-diethylbenzene) as a desorbent ("heavy" Parex™ or Eluxyl™ adsorptive separation unit) will have an extract tower to separate desorbent from the extract stream which comprises para-xylene and desorbent, finishing tower(s) to remove any other lighter hydrocarbons, such as toluene remaining from the feed, from the para-xylene, and raffinate tower(s) to separate desorbent from the raffinate stream which comprises ortho-xylene, meta-xylene, and ethylbenzene. A system comprising a Parex™ adsorptive separation unit using toluene as a desorbent ("light" Parex™ adsorptive separation unit) only needs the extract and raffinate towers, since the extract tower separates out both the toluene in the desorbent stream as well as trace toluene in the xylene feed. In a plant using both types of units the light extract tower can serve as the finishing tower for the heavy unit.

In an adsorption separation apparatus, such as a Parex™ or Eluxyl™ unit, examples of adsorbents include charcoal, ion-exchange resins, silica gel, activated carbon, zeolitic material, and the like. An adsorbent, which is particularly useful for separating para-xylene from other $C_8$ aromatics, is a faujasite-type molecular sieve material, such as zeolite X or zeolite Y, optionally, substituted or treated with an enhancing agent, such as a Group I or II element, such as potassium or barium. Examples of adsorbents for separating para-xylene from other $C_8$ aromatics are described in U.S. Pat. No. 3,761,533.

It has recently been discovered that certain Metal Organic Frameworks (MOFs) are para-xylene selective adsorbents, whereas other MOFs are ortho-xylene selective adsorbents. The para-xylene selective MOFs have a greater affinity for para-xylene than other C8 aromatics. In U.S. Pat. No. 8,704,031, two MOFs are said have excellent selectivity to para-xylene, and another MOF is said have good selectivity for ortho-xylene. The para-xylene selective MOFs are Al-MIL-53 and Zn-MOF-5. The ortho-xylene selective MOF is Cr-MIL-101. These MOF adsorbents may be used in a simulated moving bed unit. U.S. Pat. No. 8,704,031 also describes desorbents for such MOFs. Such desorbents include aromatics, such as para-diethylbenzene, toluene and 1,4-di-n-isopropylbenzene.

The isomerization step typically is accomplished by contact with a molecular sieve catalyst, such as ZSM-5, under appropriate conditions to convert a para-xylene-depleted mixture of $C_8$ aromatic hydrocarbons to thermodynamic equilibrium amounts. Historically, xylene isomerization has been accomplished in the vapor phase. However, liquid isomerization units have recently found increasing use in para-xylene separation systems.

It is known that liquid phase isomerization technology can reduce energy usage in an aromatics plant by reducing the amount of feed to vapor phase isomerization, which requires more energy due to the phase change in the isomerization process. In addition, vapor phase isomerization requires more fractionation energy in the isomerization system's heptanizer and xylene rerun tower. Further, ortho-xylene and meta-xylene in the feed may circulate, for example, at least 3.3 times through the xylene isomerization loop before being converted to para-xylene. This multiple circulation of xylenes requires large amounts of energy and, in addition, leads to xylene losses. Thus, there is an ongoing need to further improve para-xylene recovery processes to minimize energy use and maximize production.

SUMMARY OF THE INVENTION

The present invention provides a solution for the problem of excess xylene circulation through the xylene isomerization loop and associated xylene loss by using an ortho-xylene separation unit with an ortho-selective adsorbent to produce an ortho-xylene enriched stream and an ortho-xylene depleted stream. The ortho-xylene enriched stream is then isomerized over a catalyst, and the isomerate is recycled to the ortho-xylene separation unit. The ortho-xylene depleted stream is further processed to recover para-xylene product in a para-xylene separation process, such as a simulated moving bed (SMB) process. Raffinate from the para-xylene separation process, comprising meta-xylene and and ethylbenzene, may be processed over a selectivated ZSM-5 catalyst in a vapor phase unit to dealkylate the ethylbenzene without affecting the meta-xylene. After removal of lights and benzene produced from the ethylbenzene dealkylation step, the meta-xylene stream may be isomerized over a ZSM-23 catalyst to produce an isomerate stream containing higher than equilibrium concentration of para-xylene. The inventive process saves energy in multiple sections of the process by employing liquid phase isomerization, minimizing vapor phase isomerization, and reducing the volume sent to the para-xylene recovery section. Additionally, para-xylene recovery is improved over prior art processes.

In one aspect of the present invention, an aromatic hydrocarbon stream, which comprises a mixture of para-xylene, ortho-xylene, meta-xylene and ethylbenzene, is passed to an ortho-xylene separation zone to obtain a stream enriched in ortho-xylene and a stream depleted in ortho-xylene. The ortho-xylene-enriched stream is passed to a first isomerization zone to obtain a first isomerized stream having a higher concentration of para-xylene than the ortho-xylene-enriched stream, which is recycled to the ortho-xylene separation zone. The ortho-xylene-depleted stream is passed to a para-xylene separation zone to obtain a stream enriched in para-xylene and a stream depleted in para-xylene. At least a portion of the para-xylene-depleted stream is passed to an ethylbenzene conversion zone produce an ethylbenzene-depleted stream. The ethylbenzene-depleted stream is passed to a second isomerization zone to obtain second isomerized stream having a higher concentration of para-xylene than the para-xylene-depleted stream, which is recylced to the para-xylene separation zone.

In another aspect, an aromatic hydrocarbon feed stream, which comprises a mixture of para-xylene, ortho-xylene, meta-xylene and ethylbenzene, is passed to a distillation zone to separate an overhead stream comprising para-xylene, ortho-xylene, meta-xylene and ethylbenzene from a bottoms stream comprising $C_{9+}$ hydrocarbons. The overhead stream comprising para-xylene, ortho-xylene, meta-xylene and ethylbenzene is passed to an ortho-xylene separation zone comprising an ortho-xylene selective MOF to obtain an ortho-xylene-enriched stream and an ortho-xylene-depleted stream. The ortho-xylene-enriched stream is passed to a first isomerization zone conducted under liquid phase conditions to obtain a first isomerized stream having a higher concentration of para-xylene than the ortho-xylene-enriched stream, at least a portion of which is recycled to the ortho-xylene separation zone.

The ortho-xylene-depleted stream is passed to a simulated moving bed separation process comprising a para-xylene selective adsorbent to obtain a para-xylene-enriched stream and a para-xylene-depleted stream. At least a portion of the para-xylene-depleted stream is passed to an ethylbenzene conversion zone conducted under vapor phase conditions to dealkylate ethylbenzene in the para-xylene-depleted stream and produce an ethylbenzene-depleted stream. At least a portion of the ethylbenzene-depleted stream is passed to a second isomerization zone conducted under liquid phase conditions to obtain a second isomerized stream having a higher concentration of para-xylene than the para-xylene-depleted stream, which is then recycled to the distillation zone and/or the para-xylene separation zone.

DETAILED DESCRIPTION OF THE INVENTION

Figure 1:
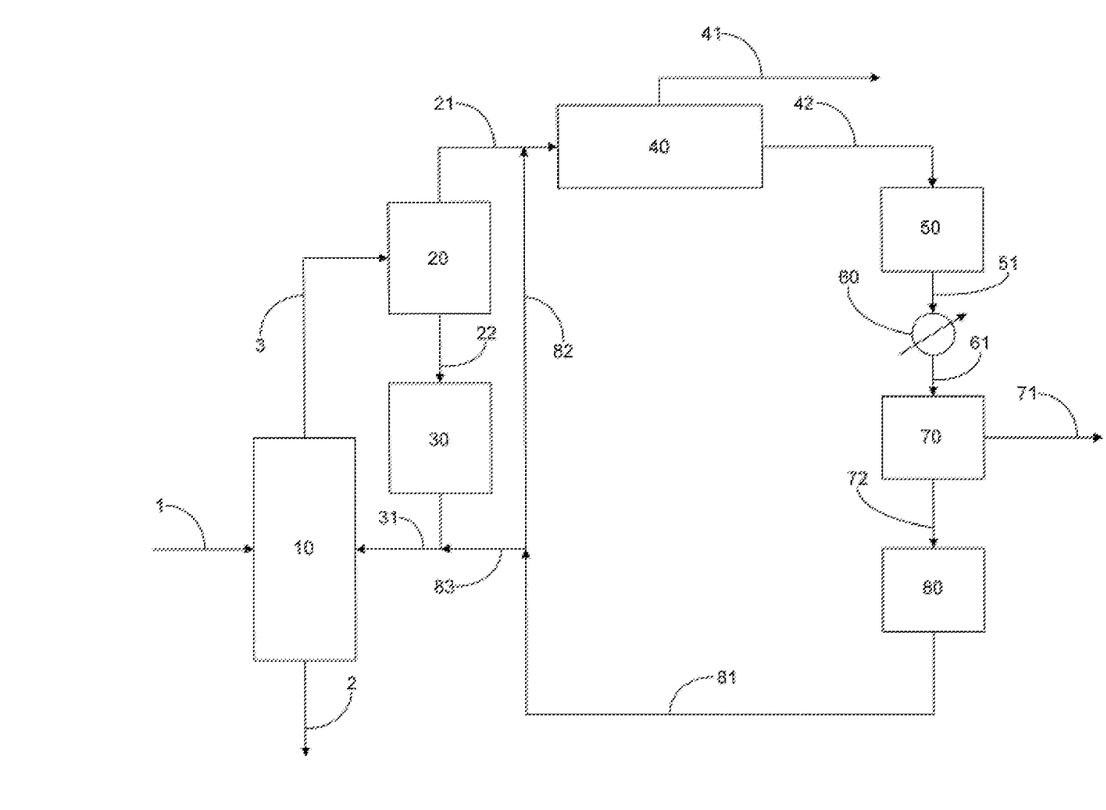
The FIGURE shows a process flow diagram for separating para-xylene from a mixture of $C_8$ aromatics.

The present invention discloses a process for producing para-xylene that removes ortho-xylene from an aromatic hydrocarbon feed by an ortho-xylene selective adsorbent, isomerizes the ortho-xylene in the liquid phase and recycles the isomerized stream. The ortho-xylene-depleted stream is passed through a para-xylene recovery section to recover para-xylene and produce a para-xylene-depleted stream, from which ethylbenzene can be removed through ethylbenzene dealkylation. The ethylbenzene-depleted stream, which comprises mostly meta-xylene, can then be isomerized in the liquid phase using a catalyst selective to the formation of para-xylene over ortho-xylene, and the isomerized stream containing para-xylene at least in its equilibrium concentration is recycled to either the ortho-xylene separation section or to the para-xylene recovery section. The inventive process saves energy in multiple sections of the process by employing liquid phase isomerization, minimizing vapor phase isomerization, and reducing the volume sent to the para-xylene recovery section.

For the purpose of this description and appended claims the following terms are defined. The term "$C_n$" hydrocarbon wherein n is a positive integer, means a hydrocarbon having n number of carbon atom(s) per molecule. The terms "$C_{n+}$" hydrocarbon and "$C_{n-}$" hydrocarbon, wherein n is a positive integer, mean a hydrocarbon having at least n number of carbon atom(s) per molecule or no more than n number of carbon atom(s) per molecule, respectively. The term "aromatics" means hydrocarbon molecules containing at least one aromatic core. The term "hydrocarbon" encompasses mixtures of hydrocarbon, including those having different values of n.

As used herein, the numbering scheme for the groups of the Periodic Table of the Elements is the current International Union of Pure and Applied Chemistry (IUPAC) number scheme.

The FIGURE shows, in a diagramatic fashion, examples of features of a process for separating para-xyxlene from a mixture of $C_8$ aromatics. In the FIGURE, an aromatic hydrocarbon feed 1 is introduced into a distillation zone 10. The aromatic hydrocarbon feed 1 includes $C_8$ aromatic hydrocarbons and may be produced by at least one refinery or petrochemical process or obtained by importing mixed xylenes. Examples of refinery or petrochemical processes for producing the feed include a reforming process, an isomerization process, a transalkylation process, a toluene disproportionation process, a benzene or toluene methylation process, and a process for converting methanol to para-xylene. In distillation zone 10, the components of the feed are separated into an overhead stream 3 including $C_8$ aromatics and bottoms stream 2 including $C_{9+}$ hydrocarbons. The aromatic hydrocarbon feed 1 may be pass through an initial separation step (not shown in the FIGURE) to remove $C_{7-}$ hydrocarbons from the feed prior to distillation zone 10.

The overhead stream 3 including $C_8$ aromatics is introduced into separation zone 20. The separation zone 20 includes an ortho-xylene selective adsorbent, such as at least one MOF. After a sufficient amount of ortho-xylene is adsorbed on the adsorbent, the adsorbent is contacted with a desorbent to form an extract stream enriched in ortho-xylene and a raffinate stream depleted in ortho-xylene. The extract stream and the raffinate stream are distilled to separate desorbent from $C_8$ aromatics and to form an ortho-xylene-enriched stream 22 and an ortho-xylene-depleted stream 21. The separation process in separation zone 20 may comprise a fixed bed or simulated moving bed adsorption process and the attendant towers for separation of desorbent from the extract and raffinate streams.

The ortho-xylene-enriched stream 22 is passed to isomerization zone 30. Ortho-xylene is isomerized in isomerization zone 30 to form a first isomerized stream 31 comprising a greater concentration of para-xylene than the ortho-xylene-enriched stream 22. At least a portion of the first isomerized stream 31 may be passed to distillation zone 10. If the first isomerized stream 31 is sufficiently devoid of $C_{9+}$ aromatics, at least a portion of this product stream may, optionally, bypass distillation zone 10 and pass directly into separation zone 20 or separation zone 40 (described below) through lines not shown in the FIGURE. The first isomerized stream 31 may also contain $C_{7-}$ hydrocarbons, which may be removed by techniques known in the art prior to recycling to the distillation zone 10, separation zone 20, or separation zone 40. The isomerization process, which takes place in isomerization zone 30, may be a vapor phase or a liquid phase process, but is preferably conducted in the liquid phase.

The ortho-xylene-depleted stream 21 is passed from separation zone 20 to separation zone 40 to produce a para-xylene-enriched stream 41 and a para-xylene-depleted stream 42. Separation zone 40 may comprise a simulated moving bed process, where the adsorbent is present in beds of a simulated moving bed unit, or a fractional crystallization process. At least a portion of the para-xylene-depleted stream 42 passes from separation zone 40 to ethylbenzene conversion zone 50. Optionally, a portion of the para-xylene-depleted stream 42 may be purged through a line not shown in the FIGURE.

Ethylbenzene is converted by a vapor phase reaction in ethylbenzene conversion zone 50 to form ethylbenzene-depleted stream 51, which is passed to heat exchanger 60. Heat exchanger 60 causes condensation of $C_8$ aromatics, and the effluent 61 from heat exchanger 60 passes to a single or multi-stage column 70. Light gases and vapors, generally $C_{6-}$ hydrocarbons, are removed from column 70 via line 71. The condensed ethylbenzene-depleted stream 72 is passed to isomerization zone 80.

In isomerization zone 80, para-xylene is fomed by isomerization of meta-xylene and/or ortho-xylene. The isomerization preferably takes place in the liquid phase, preferably in the presence of a zeolite catalyst selective to the formation of para-xylene, to produce a second isomerized stream 81 comprising a greater concentration of para-xylene than the para-xylene-depleted stream 42. In one embodiment, the second isomerized stream 81 may comprise an equilibrium mixture of $C_8$ aromatics, especially an equilibrium mixture of meta-xylene, ortho-xylene and para-xylene. In another embodiment, the second isomerized stream 81 may comprise a greater than equilibrium concentration of para-xylene.

The second isomerized stream 81 is recycled back to the distillation zone 10 via line 83, either combined with the first isomerized stream 31 or separately (not shown), or if the second isomerized stream 81 is sufficiently free of $C_{9+}$ hydrocarbons, at least a portion may pass through line 82 to separation zone 40, either combined with the ortho-xylene-depleted stream 21 or separately (not shown).

The $C_8$ Aromatic Hydrocarbon Feed

At least 50 volume percent of the $C_8$ aromatic mixture of the aromatic hydrocarbon feed 1 may be produced by at least one refinery or petrochemical process. Examples of refinery or petrochemical processes that produce equilibrium xylenes, which comprises from 15 to 30 volume percent of para-xylene based on the total volume of xylenes, include a reforming process, an isomerization process, a transalkylation process and a mixture of any of these processes. A reforming process may include passing a naphtha feed comprising $C_6$, $C_7$, and $C_8$ paraffins into a reforming unit, wherien at least a portion of the naphtha feed is converted into aromatic compounds comprising benzene, toluene, xylenes and ethylbenzene. The effluent from the reforming unit may be distilled to separate xylenes and ethylbenzene from other aromatics. A transalkylation process may comprise passing a mixture of toluene and/or benzene and $C_{9+}$ aromatic hydrocarbons (e.g., trimethylbenzene) into a transalkylation unit, which contains a transalkylation catalyst to perform the transalkylation reaction and produce $C_8$ aromatic compounds comprising xylenes and ethylbenzene. A xylenes isomerization process isomerizes a para-xylene-depleted $C_8$ aromatic hydrocarbon stream to bring the xylenes back to their equilibrium concentrations.

An example of a refinery or petrochemical process that produces para-xylene in higher than equilibrium amounts, which may comprise from 75 to 98 volume percent of para-xylene based on the total volume of xylenes, is a selective toluene disproportionation process, a selective benzene or toluene methylation process, or a selective process for converting methanol to para-xylene. These processes may be conducted in the presence of a shape selective molecular sieve catalyst. The molecular sieve may be a zeolite, for example, a medium pore size zeolite, such as ZSM-5. The molecular sieve may be treated with one or more selectivating agents, such as phosphorus or magnesium compounds, to increase the shape selectivity of the catalyst. Examples of processes for selective toluene disproportionation are described in U.S. Pat. No. 5,365,004. Examples of processes for selective toluene or benzene alkylation with a methanol alkylating agent are described in U.S. Pat. No. 6,642,426 and U.S. Publication Nos. 2015/0376086, 2015/0376087, and 2015/0376088. Examples of processes for the selective conversion of methanol to para-xylene are described in U.S. Pat. No. 4,088,706 and U.S. Publication Nos. 2015/0175498, 2015/0175499, and 2015/0175501. The selective toluene alkylation process may involve replacing at least a portion of toluene reactant with benzene and forming toluene in situ prior to converting such toluene to $C_8$ aromatics.

Ortho-Xylene Separation

Separation zone 20 contains an ortho-xylene selective adsorbent to recover the majority of ortho-xylene from the overhead stream 3 containing $C_8$ aromatics. The ortho-xylene selective adsorbent may be any ortho-xylene selective adsorbent known in the art, but in a preferred embodiment, the ortho-xylene selective adsorbent is a MOF. Metal organic frameworks or MOFs have metal ions or clusters of metal ions and organic molecules called linkers. The pores of metal organic frameworks may be used for the storage of gases, such as hydrogen and carbon dioxide. Metal organic frameworks may also be used for gas purification, gas separation, catalysis and sensors.

Metal organic framework materials are described in U.S. Pat. Nos. 5,648,508, 7,662,746 and U.S. Patent Publication No. 2009/0305040.

Various MOF materials have been developed at the Lavoisier Institute in Versailles with various phases, called "MIL" (for "Material from Institute Lavoisier"). The designation "MIL" of these structures is followed by an arbitrary number n given by inventors for identifying the different phases. Various MIL materials are described in U.S. Patent Publication No. 2015/0150981.

In addition to an MIL material, another type of MOF material is a ZIF material. ZIF stands for zeolitic imidazolate framework. These ZIF materials may be described as having a tetrahedral framework comprising a general structure, $M^1$-IM-$M^2$, wherein $M^1$ and $M^2$ comprises the same or different metal, and wherein IM is imidazolate or a substituted imidazolate linking moiety.

ZIF's include such structures iso-structural to known zeolites, for example, those identified in U.S. Patent Publication No. 2007/0202038 and U.S. Patent Publication No. 2010/037336, including ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, IHW, ISV, ITE, ITH, ITW, IWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SPE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, ZNI, and ZON. Such structures include a tetrahedral framework type selected from the group consisting of CRB, DFT, CAG, SOD, MER, RHO, ANA, LTA, DIA, ZNI, GME, LCS, FRL, GIS, POZ, MOZ. All of these framework types have been realized in the syntheses of ZIFs.

Suitable MOFs for use in separation zone 20 may be determined by testing MOFs on their ability to sorb ortho-xylene and the ability of desorbents to desorb the ortho-xylene. A suitable test method is described in an Example below. Examples of suitable ortho-xylene selective MOFs are Cr-MIL-101, which is described in U.S. Pat. No. 8,704,031, and MIL-47(V), which is described in Angew. Chem. Int. Ed. 2002; Phys. Chem. Phys., 20008, 10, 2979 and U.S. Pat. No. 9,102,609.

In the ortho-xylene separation zone, the ortho-xylene may be separated by contacting the feed with the ortho-xylene selective adsorbent to provide an adsorbent comprising adsorbed ortho-xylene. The adsorbent comprising adsorbed ortho-xylene is then contacted with a desorbent to provide a stream comprising ortho-xylene and desorbent, which may be separated by a distillation process to obtain the ortho-xylene-enriched stream.

In one embodiment, a simulated moving bed separation process may be used to separate ortho-xylene from the mixture of para-xylene, ortho-xylene, meta-xylene and ethylbenzene. In another embodiment, a fixed bed separation process, such as a process involving the use of two swing asdsorption units, may be used.

The concentration of ortho-xylene in the ortho-xylene-enriched stream may be greater than 23 wt %, and the concentration of ortho-xylene in the ortho-xylene-depleted stream may be less than 23 wt %. The concentration of ortho-xylene in the ortho-xylene-enriched stream may be at least 1.2 times greater, or at least 1.5 times greater, or at least 2.0 times greater, than the concentration of ortho-xylene in the ortho-xylene-depleted stream.

Ortho-Xylene Isomerization

Isomerization zone 30 isomerizes the ortho-xylene-enriched stream 22 to form a first isomerized stream 31 comprising a near equilibrium mixture of $C_8$ aromatics. Any prior art xylene isomerization process known to be effective for isomerizing ortho-xylene may be used, but in a preferred embodiment, the ortho-xylene-enriched stream 22 is contacted with a xylene isomerization catalyst under at least partially liquid phase conditions effective to isomerize the ortho-xylene-enriched stream 22 back towards an equilibrium concentration of the xylene isomers. Suitable conditions for the liquid phase isomerization include a temperature of from about 200° C. to about 540° C., preferably from about 230° C. to about 310° C., and more preferably from about 270° C. to about 300° C., a pressure of from about 0 to 6895 kPa(g), preferably from about 1300 kPa(g) to about 3500 kPa(g), a weight hourly space velocity (WHSV) of from 0.5 to 100 $hr^{-1}$, preferably from 1 to 20 $hr^{-1}$, and more preferably from 1 to 10 $hr^{-1}$. Generally, the conditions are selected so that at least 50 wt % of the $C_8$ aromatics would be expected to be in the liquid phase.

Any catalyst capable of isomerizing xylenes in the liquid phase can be used in the isomerization zone 30, but in one embodiment the catalyst comprises an intermediate pore size zeolite having a Constraint Index between 1 and 12. Constraint Index and its method of determination are described in U.S. Pat. No. 4,016,218, which is incorporated herein by reference. Particular examples of suitable intermediate pore size zeolites include ZSM-5, ZSM-11, ZSM-12, ZSM-22, ZSM-23, ZSM-35, ZSM-48, and MCM-22, with ZSM-5 and ZSM-11 being particularly preferred, specifically ZSM-5. It is preferred that the acidity of the zeolite, expressed as its alpha value, be greater than 300, such as greater than 500, or greater than 1000. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used to determine the alpha values cited herein include a constant temperature of 538° C. and a variable flow rate as described in detail in the Journal of Catalysis, Vol. 61, p. 395. A preferred catalyst is described in U.S. Pat. No. 8,569,559, which is incorporated herein by reference.

Para-Xylene Recovery

Separation zone 40 can include one or more of any of the para-xylene recovery units known in the art, including, for example, a crystallization unit, an adsorption unit such as a PAREX™ unit or an ELUXYL™ unit, a reactive separation unit, a membrane separation unit, an extraction unit, a distillation unit, an extractive distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984. In a preferred embodiment, separation zone 40 is a simulated moving bed or fixed bed process with a para-xylene selective adsorbent, such as a zeolite or a MOF. In the case of a MOF, suitable MOFs for adsorbing para-xylene are Al-MIL-53 and Zn-MOF-5 as described in U.S. Pat. No. 8,704,031.

After a sufficient amount of para-xylene is adsorbed on the adsorbent, the adsorbent is contacted with a desorbent to form an extract stream enriched in para-xylene and a raffinate stream depleted in para-xylene. The extract stream and the raffinate stream are distilled to separate out the desorbent and to form a para-xylene-enriched stream 41 and a para-xylene-depleted stream 42. In one embodiment, the para-xylene-enriched stream 41 comprises at least 50 wt % para-xylene, preferably at least 60 wt % para-xylene, more preferably at least 70 wt % para-xylene, even more preferably at least 80 wt % para-xylene, most preferably at least 90 wt % para-xylene, and ideally at least 95 wt % para-xylene, based on the total weight of the para-xylene rich product stream. The para-xylene-depleted stream 42 comprises ethylbenzene, meta-xylene, and a small amount of ortho-xylene that was not removed by separation zone 20.

Ethylbenzene Removal

At least a portion of the para-xylene-depleted stream 42 passes from separation zone 40 to ethylbenzene conversion zone 50 where para-xylene-depleted stream 42 is contacted with a xylene isomerization catalyst under at least partially vapor phase conditions effective to convert the ethylbenzene. There are generally two types of vapor phase isomerization catalysts—one that dealkylates ethylbenzene to produce benzene and ethylene, and one that isomerizes the four different $C_8$ aromatic compounds, including ethylbenzene, to their equilibrium concentrations. Either catalyst may be used for the ethylbenzene conversion zone 50, but in a preferred embodiment, a catalyst effective to dealkylate the ethylbenzene and form benzene by cracking/disproportionation is used.

Ethylbenzene Dealkylation

The ethylbenzene dealkylation catalyst typically comprises an intermediate pore size zeolite having a Constraint Index ranging from 1 to 12, a silica to alumina molar ratio of at least about 5, such as at least about 12, for example, at least 20, and an alpha value of at least 5, such as 75 to 5000. Constraint Index and its method of determination are disclosed in U.S. Pat. No. 4,016,218, which is herein incorporated by reference, whereas the alpha test is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

Examples of suitable intermediate pore size zeolites include: ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); ZSM-58 (U.S. Pat. No. 4,417,780); EU-1; and mordenite. The entire contents of the above references are incorporated by reference herein. Preferred zeolites are ZSM-5, ZSM-12 or EU-1.

The zeolite employed in ethylbenzene dealkylation catalyst typically has a crystal size of at least 0.2 microns and exhibits an equilibrium sorption capacity for xylene, which can be either para, meta, ortho, or a mixture thereof, of at least 1 gram per 100 grams of zeolite measured at 120° C. and a xylene pressure of 4.5+0.8 mm of mercury and an ortho-xylene sorption time for 30 percent of its equilibrium ortho-xylene sorption capacity of greater than 1200 minutes (at the same conditions of temperature and pressure). The sorption measurements may be carried out gravimetrically in a thermal balance. The sorption test is described in U.S. Pat. Nos. 4,117,026; 4,159,282; 5,173,461; and Re. 31,782, each of which is incorporated by reference herein.

The zeolite used in the ethylbenzene dealkylation catalyst may be self-bound (no binder) or may be composited with an inorganic ortho-xyleneide binder, with the zeolite content ranging from between about 1 to about 99 percent by weight and more usually in the range of about 10 to about 80 percent by weight of the dry composite, e.g., about 65% zeolite with about 35% binder. Where a binder is used, it is preferably non-acidic, such as silica. Procedures for preparing silica bound ZSM-5 are described in U.S. Pat. Nos. 4,582,815; 5,053,374; and 5,182,242, incorporated by reference herein.

In addition, the ethylbenzene dealkylation catalyst typically comprises from about 0.001 to about 10 percent by weight, e.g., from about 0.05 to about 5 percent by weight, e.g., from about 0.1 to about 2 percent by weight of a hydrogenation/dehydrogenation component. Examples of such components include the ortho-xyleneide, hydrortho-xyleneide, sulfide, or free metal (i.e., zero valent) forms of Group VIIIA metals (i.e., Pt, Pd, Ir, Rh, Os, Ru, Ni, Co, and Fe), Group VIIA metals (i.e., Mn, Tc, and Re), Group VIA metals (i.e., Cr, Mo, and W), Group VB metals (i.e., Sb and Bi), Group IVB metals (i.e., Sn and Pb), Group IIIB metals (i.e., Ga and In), and Group IB metals (i.e., Cu, Ag, and Au). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The metal may be in a reduced valence state, e.g., when this component is in the form of an ortho-xyleneide or hydrortho-xyleneide. The reduced valence state of this metal may be attained, in situ, during the course of a reaction, when a reducing agent, such as hydrogen, is included in the feed to the reaction.

Using the catalyst system described above, ethylbenzene cracking/disproportionation is typically effected at conditions including a temperature of from about 400° F. to about 1,000° F. (204 to 538° C.), a pressure of from about 0 to about 1,000 psig (100 to 7,000 kPa), a weight hourly space velocity (WHSV) of between about 0.1 and about 200 $hr^{-1}$, and a hydrogen, $H_2$, to hydrocarbon, HC, molar ratio of between about 0.1 and about 10. Alternatively, the conversion conditions may include a temperature of from about 650° F. and about 900° F. (343 to 482° C.), a pressure from about 50 and about 400 psig (446 to 2,859 kPa), a WHSV of between about 3 and about 50 hr$^{-1}$ and a H$_2$ to HC molar ratio of between about 0.5 and about 5. The WHSV is based on the weight of catalyst composition, i.e., the total weight of active catalyst plus, if used, binder.

EB Isomerization

Typically, the ethylbenzene isomerization catalyst comprises an intermediate pore size molecular sieve having a Constraint Index within the approximate range of 1 to 12, such as ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). Alternatively, the ethylbenzene isomerization catalyst may comprise a molecular sieve selected from MCM-22 (described in U.S. Pat. No. 4,954,325); PSH-3 (described in U.S. Pat. No. 4,439,409); SSZ-25 (described in U.S. Pat. No. 4,826,667); MCM-36 (described in U.S. Pat. No. 5,250,277); MCM-49 (described in U.S. Pat. No. 5,236,575); and MCM-56 (described in U.S. Pat. No. 5,362,697). The molecular sieve may also comprise a EUO structural type molecular sieve, with EU-1 being preferred, or mordenite. A preferred molecular sieve is one of the EUO structural type having a Si/Al ratio of about 10-25, as disclosed in U.S. Pat. No. 7,893,309. The entire contents of the above references are incorporated by reference herein.

It may be desirable to combine the molecular sieve of the ethylbenzene isomerization catalyst with another material resistant to the temperature and other conditions of the process. Such matrix materials include synthetic or naturally occurring substances as well as inorganic materials such as clay, silica, and/or metal oxides (such as titanium oxide or boron oxide). The metal oxides may be naturally occurring or in the form of gelatinous precipitates or gels including mixtures of silica and metal oxides. Naturally occurring clays, which can be composited with the molecular sieve, include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the molecular sieve may be composited with a porous matrix material, such as alumina, zirconia, silica-alumina, silica-magnesia, silica-zirconia, silica-thoria, silica-berylia, silica-titania, aluminum phosphates, titanium phosphates, zirconia phosphates, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

The ethylbenzene isomerization catalyst also comprises at least one metal from Group VIII of the periodic table of the elements and optionally at least one metal selected from metals from Groups IIIA, IVA, and VIIB. The Group VIII metal present in the catalyst used in the isomerization process of the invention is selected from iron, cobalt, nickel, ruthenium, rhodium, palladium, osmium, iridium, and platinum, preferably from the noble metals and highly preferably from palladium and platinum. More preferably, the Group VIII metal is platinum. The metal selected from groups IIIA, IVA, and VIIB which are optionally present is selected from gallium, indium, tin, and rhenium, preferably from indium, tin, and rhenium.

The conditions employed in the ethylbenzene isomerization process generally include a temperature of from 300 to about 500° C., preferably from about 320 to about 450° C. and more preferably from about 340 to about 430° C.; a partial pressure of hydrogen from about 0.3 to about 1.5 MPa, preferably from about 0.4 to about 1.2 MPa, and more preferably from about 0.7 to about 1.2 Mpa; a total pressure of from about 0.45 to about 1.9 MPa, preferably from about 0.6 to about 1.5 MPa; and a weight hourly space velocity (WHSV) of between about 0.25 and about 30 hr$^{-1}$, preferably between about 1 and about 10 hr$^{-1}$ and more preferably between about 2 and about 6 hr$^{-1}$.

The effluent from ethylbenzene conversion zone 50, ethylbenzene-depleted stream 51, contains benzene, light gases such as ethylene and ethane from the hydrocracking reaction, meta-xylene and ortho-xylene. The ethylbenzene-depleted stream 51 may be passed to heat exchanger 60 to condense the C$_8$ aromatics, while retaining benzene and lesser boiling compounds (i.e., compounds have a boiling point less than the boiling point of benzene), such as ethane, in the vapor state. The effluent 61 from heat exchanger 60 passes to a single or multi-stage column 70, which removes the light gases and vapors, generally C$_{6-}$ hydrocarbons, via line 71. The condensed ethylbenzene-depleted stream 72 is then passed to isomerization zone 80.

Meta-Xylene Isomerization

The condensed ethylbenzene-depleted stream 72 comprises mostly meta-xylene, as ortho-xylene has been removed by separation zone 20, para-xylene has been recovered in separation zone 40, and ethylbenzene has been removed by ethylbenzene conversion zone 50. Isomerization zone 80 may contain any known isomerization catalyst effective to isomerize C$_8$ aromatics, but in a preferred embodiment, a catalyst, which selectively isomerizes meta-xylene to para-xylene, is used to produce a second isomerized stream 81 that comprises a greater than equilibrium concentration of para-xylene.

The isomerization of xylenes to selectively produce para-xylene over a ZSM-23 catalyst is described in U.S. Provisional Application No. 62/267,428. The ZSM-23 may have a SiO$_2$/Al$_2$O$_3$ ratio between 15-75, preferably between 15-50, an external surface area of at least 75 m$^2$/g, preferably at least 90 m$^2$/g, most preferably about 105 to 115 m$^2$/g, and an average crystal size of 5 microns or less, or 2 microns or less, or 1 micron or less, or 0.1 microns or less, such as that disclosed in U.S. Pat. Nos.: 5,332,566; 4,599,475; and 4,531,012, which are all incorporated herein by reference in their entireties.

External surface area may be calculated using the Brunauer-Emmett-Teller (BET) method. In the Brunauer-Emmett-Teller (BET) method, the overall surface area (also referred to as total surface area) of a molecular sieve may be measured using the adsorption-desorption of nitrogen by a solid at 77 K as the function of relative partial pressure. The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

Particle size is measured by averaging the size of multiple particles as shown in SEM images obtained on a HITACHI S4800 Field Emission Scanning Electron Microscope (SEM). The particle size is measured by averaging the size of multiple particles as shown in the SEM. The same method is used for crystal size. Transmission Electron Microscopy may also be used, but in event of conflict between SEM and TEM, SEM shall control.

In one embodiment, the ZSM-23 is self-bound. In another embodiment, the ZSM-23 may include one or more binder or matrix materials resistant to the temperatures and other conditions employed in the process. Such materials include materials such as clays, silica, and/or metal ortho-xyleneides such as alumina. The relative proportions of porous crystalline material and optional inorganic ortho-xyleneide matrix vary widely, with the content of the porous crystalline material ranging from about 1 to about 90% by weight, and more usually in the range of about 2 to about 80 wt % of the composite. In an embodiment in which the catalyst composition includes an inorganic ortho-xyleneide matrix material, the matrix material preferably comprises about 35 wt % of alumina binder (making the balance of the catalyst comprise about 65 wt % ZSM-23).

This ZSM-23 catalyst may convert meta-xylene to para-xylene while forming only a small amount of ortho-xylene. This ZSM-23 cataylst may produce a higher than equilibrium amount of para-xylene, e.g., more than about 24 wt % of para-xylene, based on the total amount of xylenes. In one embodiment, the second isomerized stream 81 contains at least about 27 wt % para-xylene, based on the total amount of xylenes. Preferably, the catalyst produces para-xylene at a ratio of meta-xylene:para-xylene of about 2:1, minimal ethylbenzene, minimal ortho-xylene, and minimal $C_{9+}$ aromatics.

Isomerization zone 80 is typically operated at conditions including a temperature of from about 400° F. (about 204° C.) to about 1,000° F. (about 538° C.), preferably from about 482° F. (250° C.) to about 572° F. (300° C.), more preferably about 482° F. (250° C.) to about 527° F. (275° C.); a pressure of from about 0 to 1,000 psig (6.9 MPa), preferably from about 350 psig (2.41 MPa) to about 500 psig (3.45 MPa), more preferably about 350 psig (2.41 MPa) to about 400 psig (2.75 MPa); and a weight hourly space velocity (WHSV) of from 0.5 to 100 $hr^{-1}$, preferably from 0.5 to 10 $hr^{-1}$, more preferably from 0.5 to 5 $hr^{-1}$, with the pressure and temperature being adjusted within the above ranges to ensure that at least part of the condensed ethylbenzene-depleted stream 72 is in the liquid phase. Generally, the conditions are selected so that at least 50 wt % of the condensed ethylbenzene-depleted stream 72 would be expected to be in the liquid phase.

The present invention saves energy by minimizing the use of vapor phase isomerization due to the availability of liquid phase isomerizaiton for the ortho-xylene-enriched stream 22 and the condensed ethylbenzene-depleted stream 72. Additionally, by removing ortho-xylene prior to para-xylene recovery and the use of a catalyst that selectively isomerizes meta-xylene to para-xylene, less recycle of xylenes is necessary in the xylenes loop, resulting in reduced xylene losses. Further, decreasing the volume of the stream sent to the para-xylene recovery section also saves energy.

The present invention also increases overall para-xylene recovery. In a standard xylenes loop including a SMB process, isomerization (liquid phase or vapor phase) and a distillation zone to separate out $C_{9+}$ aromatics, the para-xylene recovery is typically about 23%. However, using the process described in the FIGURE, with the ortho-xylene separation zone 20 and isomerization zone 30, the para-xylene recovery is 30-33%.

The invention will now be more particularly described with reference to the following non-limiting Example.

EXAMPLE

A mixture of xylenes containing para-xylene, meta-xylene, ortho-xylene and ethylbenzene was passed over the adsorbent (zeolite or MOF) pre-saturated with the desorbent at various temperatures. Once the adsorption was complete, as evident from breakthrough of the strongest adsorbed component and effluent composition reaching the feed composition, the bed was subject to a desorbent to remove the adsorbed species. The process was repeated over 3 adsorption-desorption cycles.

Using the above test procedure, MIL-47 (V) was tested using n-heptane as a desrbent. MIL-47 (V) is described in Angew. Chem. Int. Ed. 2002; Phys. Chem. Phys., 20008, 10, 2979. The synthesis of MIL-47 (V) is also described in U.S. Pat. No. 9,102,609. Results of this test are summarized in Table 1. The results of this test demonstrate that MIL-47 (V) is an ortho-selective adsorbent.

TABLE 1

| Material | Breakthrough Temperature [° C.] | Capacity [mmol/g] | OX/EB | OX/MX | OX/PX |
|---|---|---|---|---|---|
| MIL-47 (V) | 50 | 4.5 | 2.1 | 1.4 | 1.4 |
| Heptane Desorbent | 100 | 4.3 | 3.2 | 2.1 | 1.9 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing para-xylene from a mixture comprising para-xylene, ortho-xylene, meta-xylene and ethylbenzene, said process comprising:
   (a) passing an aromatic hydrocarbon feed stream, which comprises a mixture of para-xylene, ortho-xylene, meta-xylene and ethylbenzene, to an ortho-xylene separation zone to obtain an ortho-xylene-enriched stream and an ortho-xylene-depleted stream;
   (b) passing the ortho-xylene-enriched stream to a first isomerization zone to obtain a first isomerized stream having a higher concentration of para-xylene than the ortho-xylene-enriched stream;
   (c) recycling at least a portion of the first isomerized stream to the ortho-xylene separation zone of step (a);
   (d) passing the ortho-xylene-depleted stream to a para-xylene separation zone to obtain a para-xylene-enriched stream and a para-xylene-depleted stream;
   (e) passing at least a portion of the para-xylene-depleted stream to an ethylbenzene conversion zone to produce an ethylbenzene-depleted stream;
   (f) passing at least a portion of the ethylbenzene-depleted stream to a second isomerization zone to obtain a second isomerized stream having a higher concentration of para-xylene than the para-xylene-depleted stream; and
   (g) passing at least a portion of the second isomerized stream to the para-xylene separation zone.

2. The process of claim 1, wherein ortho-xylene is separated from the mixture of para-xylene, ortho-xylene, meta-xylene and ethylbenzene in the ortho-xylene separation zone of step (a) by a process comprising:
   (i) adsorbing ortho-xylene in the mixture on an ortho-xylene selective adsorbent to provide an adsorbent comprising adsorbed ortho-xylene;
   (ii) contacting the adsorbent comprising adsorbed ortho-xylene from step (i) with a desorbent to provide a stream comprising ortho-xylene and desorbent; and
   (iii) separating the ortho-xylene from the desorbent by a distillation process to obtain the ortho-xylene-enriched stream.

3. The process of claim 2, wherein the ortho-xylene selective adsorbent comprises a Metal Organic Framework.

4. The process of claim 3, wherein the Metal Organic Framework is Cr-MIL-101 or MIL-47 (V).

5. The process of claim 1, wherein a simulated moving bed separation process is used to separate ortho-xylene from the mixture of para-xylene, ortho-xylene, meta-xylene and ethylbenzene in step (a).

6. The process of claim 1, wherein a simulated moving bed separation process is used to separate para-xylene from the ortho-xylene-depleted stream in step (d).

7. The process of claim 1, wherein a zeolite is used as an adsorbent in step (d).

8. The process of claim 1, further comprising passing the ethylbenzene-depleted stream from step (e) through a heat exchanger to condense $C_8$ aromatics in the ethylbenzene-depleted stream, separating $C_6$-hydrocarbons from the condensed $C_8$ aromatics to produce a condensed ethylbenzene-depleted stream, and passing the condensed ethylbenzene-depleted stream to step (f).

9. The process of claim 1, wherein, prior to step (a), a raw aromatic hydrocarbon feed stream is passed to a distillation zone to separate an overhead stream comprising para-xylene, ortho-xylene, meta-xylene and ethylbenzene from a bottoms stream comprising $C_{9+}$ hydrocarbons, and wherein at least a portion of the overhead stream is passed as the aromatic hydrocarbon feed stream to the ortho-xylene separation zone of step (a).

10. The process of claim 1, wherein the first isomerization zone of step (b) is conducted in a liquid phase.

11. The process of claim 1, wherein the ethylbenzene conversion zone of step (e) is conducted in a vapor phase and comprises dealkylating the ethylbenzene in the para-xylene-depleted stream.

12. The process of claim 1, wherein the ethylbenzene conversion zone of step (e) is conducted in a vapor phase and comprises isomerizing the ethylbenzene in the para-xylene-depleted stream.

13. The process of claim 1, wherein the second isomerization zone of step (f) is conducted in a liquid phase.

14. The process of claim 1, wherein the second isomerization zone contains a catalyst comprising a ZSM-23 with a $SiO_2/Al_2O_3$ ratio between 15-75, an external surface area of at least 75 $m^2/g$, and an average crystal size of 5 microns or less.

15. A process for producing para-xylene from a mixture comprising para-xylene, ortho-xylene, meta-xylene and ethylbenzene, said process comprising:
   (a) passing an aromatic hydrocarbon feed stream, which comprises a mixture of para-xylene, ortho-xylene, meta-xylene and ethylbenzene, to a distillation zone to separate an overhead stream comprising para-xylene, ortho-xylene, meta-xylene and ethylbenzene from a bottoms stream comprising $C_{9+}$ hydrocarbons;
   (b) passing the overhead stream comprising para-xylene, ortho-xylene, meta-xylene and ethylbenzene to an ortho-xylene separation zone comprising an ortho-xylene selective Metal Organic Framework to obtain an ortho-xylene-enriched stream and an ortho-xylene-depleted stream;
   (c) passing the ortho-xylene-enriched stream to a first isomerization zone conducted under liquid phase conditions to obtain a first isomerized stream having a higher concentration of para-xylene than the ortho-xylene-enriched stream;
   (d) recycling at least a portion of the first isomerized stream to the ortho-xylene separation zone of step (b);
   (e) passing the ortho-xylene-depleted stream to a simulated moving bed separation process comprising a para-xylene selective adsorbent to obtain a para-xylene-enriched stream and a para-xylene-depleted stream;
   (f) passing at least a portion of the para-xylene-depleted stream to an ethylbenzene conversion zone conducted under vapor phase conditions to dealkylate ethylbenzene in the para-xylene-depleted stream and produce an ethylbenzene-depleted stream;
   (g) passing at least a portion of the ethylbenzene-depleted stream to a second isomerization zone conducted under liquid phase conditions to obtain a second isomerized stream having a higher concentration of para-xylene than the para-xylene-depleted stream; and
   (h) passing at least a portion of the second isomerized stream to the distillation zone of step (a) and/or the simulated moving bed separation process of step (e).

16. The process of claim 15, wherein step (b) comprises contacting the overhead stream comprising para-xylene, ortho-xylene, meta-xylene and ethylbenzene with the ortho-xylene selective Metal Organic Framework, followed by contacting the the ortho-xylene selective Metal Organic Framework with a desorbent to form an extract comprising ortho-xylene and desorbent, and distilling the extract to remove desorbent and produce the ortho-xylene-enriched stream.

17. The process of claim 16, wherein the desorbent is a non-aromatic hydrocarbon having 7 or less carbon atoms.

18. The process of claim 17, wherein the desorbent is n-heptane.

19. The process of claim 15, wherein the ortho-xylene selective Metal Organic Framework is MIL-47 (V).

20. The process of claim 15, wherein a simulated moving bed separation process is used to separate ortho-xylene from the mixture of para-xylene, ortho-xylene, meta-xylene and ethylbenzene in step (b).

21. The process of claim 15, further comprising passing the ethylbenzene-depleted stream from step (f) through a heat exchanger to condense $C_8$ aromatics in the ethylbenzene-depleted stream, separating $C_6$-hydrocarbons from the condensed $C_8$ aromatics to produce a condensed ethylbenzene-depleted stream, and passing the condensed ethylbenzene-depleted stream to step (g).

22. The process of claim 15, wherein the second isomerization zone contains a catalyst comprising a ZSM-23 with a $SiO_2/Al_2O_3$ ratio between 15-75, an external surface area of at least 75 $m^2/g$, and an average crystal size of 5 microns or less.

* * * * *